United States Patent
Oel

(10) Patent No.: US 10,806,350 B2
(45) Date of Patent: Oct. 20, 2020

(54) SENSOR SYSTEM FOR OCCUPANT SUPPORT

(71) Applicant: Faurecia Automotive Seating, LLC, Auburn Hills, MI (US)

(72) Inventor: Ludger Oel, Stadthagen (DE)

(73) Assignee: Faurecia Automotive Seating, LLC, Auburn Hills, MI (US)

( * ) Notice: Subject to any disclaimer, the term of this patent is extended or adjusted under 35 U.S.C. 154(b) by 181 days.

(21) Appl. No.: 16/019,915

(22) Filed: Jun. 27, 2018

(65) Prior Publication Data
US 2020/0000344 A1    Jan. 2, 2020

(51) Int. Cl.
| *A61B 5/0205* | (2006.01) |
| *A61B 5/0428* | (2006.01) |
| *A61B 5/1455* | (2006.01) |
| *A61B 5/00* | (2006.01) |
| *B60H 1/00* | (2006.01) |

(52) U.S. Cl.
CPC ........ *A61B 5/0205* (2013.01); *A61B 5/04284* (2013.01); *A61B 5/14552* (2013.01); *A61B 5/6893* (2013.01); *B60H 1/00742* (2013.01)

(58) Field of Classification Search
CPC ..... A61B 5/18; A61B 5/0205; A61B 5/04284; A61B 5/14552; A61B 5/6893; B60H 1/00742
USPC ................................ 600/509; 340/73, 539.1
See application file for complete search history.

(56) References Cited

U.S. PATENT DOCUMENTS

| 984,881 | A |   | 2/1911 | Bender |
| 8,255,042 | B2 |   | 8/2012 | MacQuarrie |
| 8,706,204 | B2 |   | 4/2014 | Seo |
| 9,215,991 | B2 |   | 12/2015 | Inan |
| 2007/0073175 | A1 | * | 3/2007 | McAtamney ...... A61B 5/04282 600/509 |
| 2016/0051156 | A1 | * | 2/2016 | Kim ..................... A61B 5/0205 600/391 |
| 2016/0354027 | A1 | * | 12/2016 | Benson ................. A61M 21/02 |
| 2017/0360373 | A1 |   | 12/2017 | Montgomery |

FOREIGN PATENT DOCUMENTS

| WO | 2013128364 | 9/2013 |
| WO | 2018009165 | 1/2018 |

OTHER PUBLICATIONS

The Smart Car Seat: Personalized Monitoring of Vital Signs in Automotive Applications (2011) (https://link.springer.com/article/10.1007/s00779-010-0350-4), 12 pages.
A Smart Health Monitoring Chair for Nonintrusive Monitoring of Biological Signals (2011) (https://ieeexplore.ieee.org/abstract/document/6078433/), 6 pages.

* cited by examiner

*Primary Examiner* — Erin M Piateski
(74) *Attorney, Agent, or Firm* — Barnes & Thornburg LLP

(57) ABSTRACT

An occupant support includes a vehicle seat and a sensor system coupled to the vehicle seat. The sensor system is configured to provide biometric data of an occupant of the vehicle seat.

9 Claims, 3 Drawing Sheets

SENSOR SYSTEM FOR OCCUPANT SUPPORT

BACKGROUND

The present disclosure relates to sensor systems for use with occupant supports. More particularly, the present disclosure relates to piezoelectric and capacitive sensor systems.

SUMMARY

According to the present disclosure, an occupant support includes a vehicle seat and a sensor system coupled to the vehicle seat. The sensor system is configured to provide biometric data of an occupant of the vehicle seat.

In illustrative embodiment, the biometric data includes piezoelectric sensor data and capacitive sensor data. The sensor system includes a first sensor including a first metallic electrode, a second metallic electrode, and a piezoelectric element positioned between the first metallic electrode and the second metallic electrode.

In illustrative embodiments, the piezoelectric sensor data includes ballistocardiogram data or sound data. In illustrative embodiments, the piezoelectric sensor data is indicative of a voltage across the piezoelectric element between the first metallic electrode and the second metallic electrode.

In illustrative embodiments, the capacitive sensor data includes electrocardiogram data. In illustrative embodiments, the capacitive sensor data is indicative of capacitive coupling between the first metallic electrode and the occupant of the vehicle seat. In illustrative embodiments the sensor system includes a second sensor including a first metallic electrode, a second metallic electrode, and a piezoelectric element positioned between the first metallic electrode and the second metallic electrode, and the capacitive sensor data is indicative of a first voltage between the first metallic electrode of the first sensor and the first metallic electrode of the second sensor. In illustrative embodiments, the first voltage is galvanically isolated from a second voltage across the piezoelectric element of the first sensor. In illustrative embodiments, the sensor system is configured to short the first metallic electrode and the second metallic electrode in a capacitive sensing mode.

According to the present disclosure, a method for measuring biometric data of an occupant of a vehicle seat includes measuring piezoelectric sensor data with a sensor system coupled to the vehicle seat, wherein the sensor system comprises a first sensor including a first metallic electrode, a second metallic electrode, and a piezoelectric element positioned between the first metallic electrode and the second metallic electrode, and wherein the piezoelectric sensor data is indicative of voltage across the piezoelectric element, and measuring capacitive sensor data with the sensor system, wherein the capacitive sensor data is indicative of capacitive coupling between the first metallic electrode and the occupant of the vehicle seat. In illustrative embodiments, measuring the capacitive sensor data includes shorting the first metallic electrode and the second metallic electrode. In illustrative embodiments, the method further includes combining the piezoelectric sensor data and the capacitive sensor data to generate biomedical data of the occupant.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

DETAILED DESCRIPTION

Figure 1:
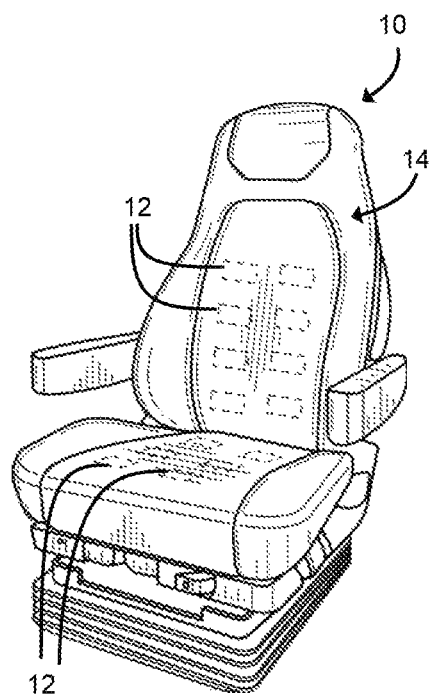
FIG. 1 is a perspective and diagrammatic view of a sensor system in accordance with the present disclosure coupled to an occupant support suggesting that the sensor system includes a plurality of sensors configured to measure physiological data of an occupant positioned on the occupant support and a control system coupled to the sensors.
Figure 2:
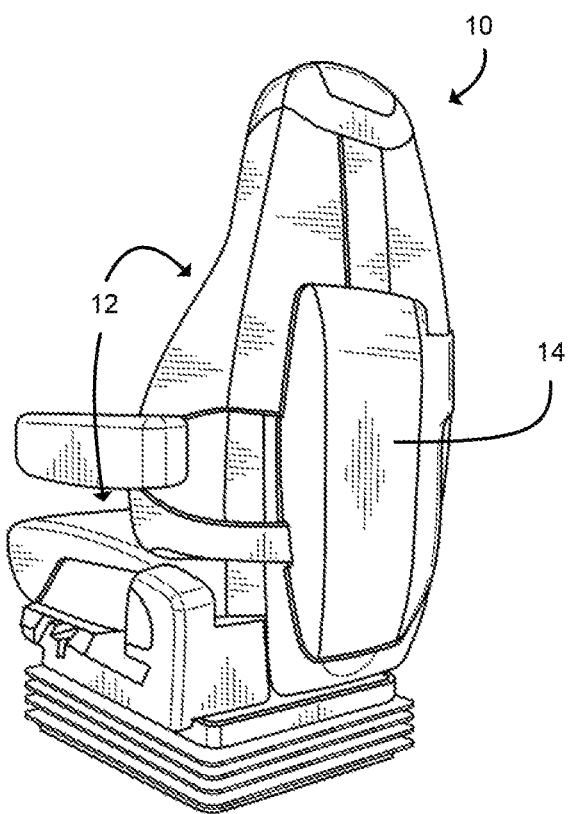
FIG. 2 is a rear perspective view of the sensor system in coupled to the occupant support showing the control system housed in a back of the occupant support.

A sensor system 14 in accordance with the present disclosure is adapted for use with an occupant support 10 such as, for example, a seat as shown in FIGS. 1 and 2. Occupant support 10 may be included in a vehicle or occupant support 10 may be any occupant support 10 configured to support an occupant.

As shown in FIGS. 1 and 2, the occupant support 10 includes a plurality of sensors 12 which may be configured to measure occupant physiology and surrounding environment information. The sensors 12 may be incorporated in or otherwise attached to one or more comfort layers of the occupant support 10 or otherwise incorporated in the occupant support 10. Illustratively, the sensors 12 are spaced apart from each other and located in a bottom cover and a back cover of the occupant support 10. Additionally, the occupant support 10 may include a different number and/or arrangement of sensors 12. Sensor system 14 receives signals from the sensors 12. The sensor system 14 may determine occupant health data indicative of physiological characteristics of an occupant and/or occupant state data indicative of a state of the occupant based on signals from the sensors 12.

Figure 3:
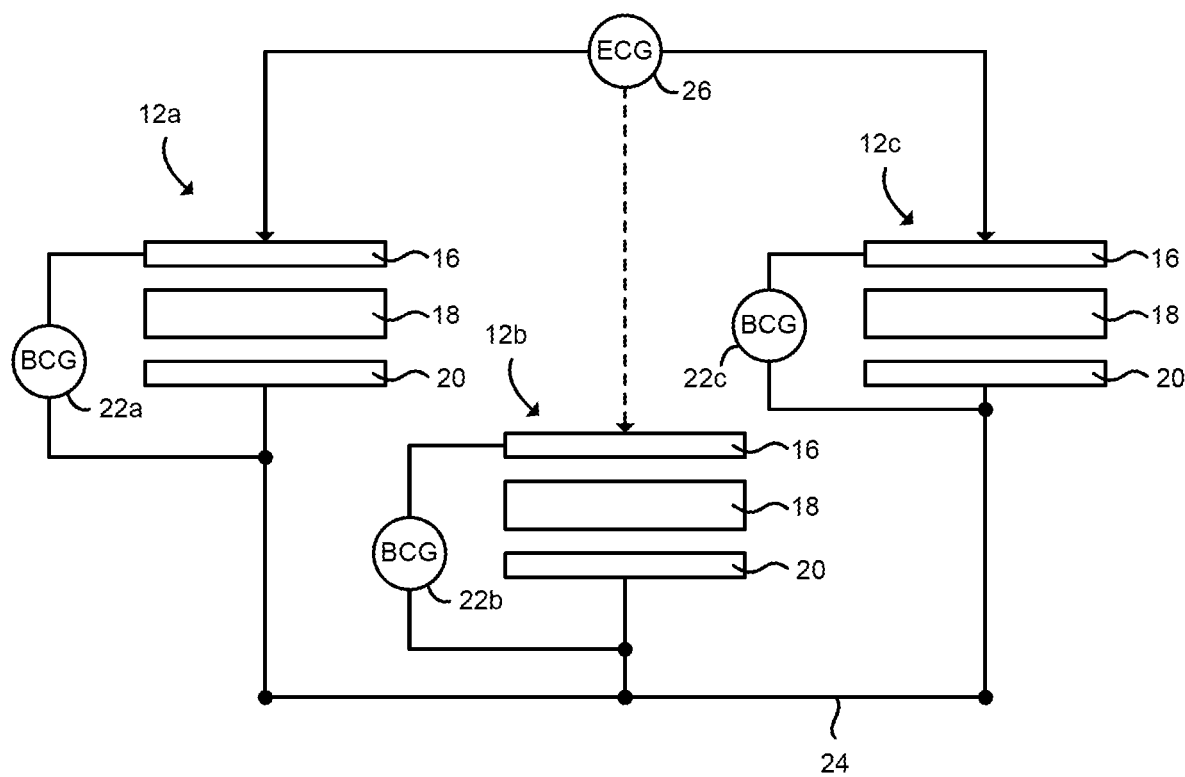
FIG. 3 is a diagrammatic view of the sensor system of FIGS. 1 and 2.

Referring now to FIG. 3, three illustrative sensors 12a, 12b, 12c are shown. Each sensor 12 includes a top electrode 16, a piezoelectric element 18, and a bottom electrode 20. Each of the electrodes 16, 20 may be embodied as a metallic plate or other conductive element. In some embodiments, although illustrated as a top electrode 16 and a bottom electrode 20, the electrodes 16, 20 may be installed in any orientation. The piezoelectric element 18 is positioned between and in contact with the electrodes 16, 20 and may be embodied as a piezoelectric foil or other element that includes a piezoelectric material. Illustratively, the piezoelectric element 18 includes a piezoelectric foil made of polyvinylidene fluoride (PVDF). The piezoelectric element 18 creates an output voltage that depends on the dynamical force/pressure change acting on the piezoelectric element 18.

As shown, each of the sensors 12a, 12b, 12c is coupled to a corresponding ballistocardiography (BCG) unit 22a, 22b, 22c, respectively. The bottom electrode 20 of each sensor 12 is connected to a common BCG ground 24. The BCG units 22 may be embodied as or otherwise incorporated in any microcontroller, microprocessor, system-on-a-chip (SoC), electronic control unit (ECU), digital signal processor, or other control circuit and related electronics (e.g., analog/digital inputs, signal conditioning stages, amplifiers, and/or other circuitry) capable of performing the operations described herein. In some embodiments, the BCG units 22 may be included in, coupled with, or otherwise controlled by the sensor system 14.

Each BCG unit 22 measures the voltage across the corresponding sensor 12, which depends on mechanical deformation of the sensor 12. For example, based on force/pressure changes applied to the piezoelectric element 18, a charge is generated, which may be measured with a charge mode amplifier. The sensor data measured by each BCG unit 22 may be indicative of biomedical data such as a heart rate or respiration rate of an occupant of the vehicle support 10. For example, the sensor data may be indicative of micro movements caused by blood pulsations. As another example, the sensor data measured by each BCG unit 22 may be indicative of sound vibrations experienced by the sensor 12.

As shown, the top electrode 16 of each of the sensors 12a, 12b, 12c is coupled to an electrocardiography (ECG) unit 26. Similar to the BCG units 22, the ECG unit 26 may be embodied as or otherwise incorporated in any microcontroller, microprocessor, system-on-a-chip (SoC), electronic control unit (ECU), digital signal processor, or other control circuit and related electronics (e.g., analog/digital inputs, signal conditioning stages, amplifiers, and/or other circuitry) capable of performing the operations described herein. In some embodiments, the ECG unit 26 may be included in, coupled with, or otherwise controlled by the sensor system 14.

The ECG unit 26 measures the voltage difference between top electrodes 16 of different sensors 12. Illustratively, the ECG unit 26 measures the voltage difference between the top electrodes 16 of the sensors 12a, 12c as compared to a reference voltage measured at sensor 12b. The measured voltage of the top electrodes 16 is indicative of voltage transferred from the skin of an occupant of the occupant support 10 and the top electrode 16 through capacitive coupling. In that configuration, the skin of the occupant and the top electrode 16 operate as plates of a capacitor, and the material between the skin of the occupant and the top electrode 16 (e.g., clothing, vehicle seat trim, air, etc.) operate as a dielectric of the capacitor. The sensor data measured by the ECG unit 26 is thus indicative of voltage differences between different locations on the occupant's skin, which may be indicative of biomedical data such as the heart rate and/or respiration rate of the user.

Signals measured by the BCG units 22 and ECG unit 26 may be isolated to prevent interaction, which may prevent piezoelectric voltages from dominating capacitive voltages. In some embodiments, signal conditioning stages of the BCG units 22 may be galvanically isolated from a signal conditioning stage of the ECG unit 26, so that piezoelectric voltages (e.g., voltages across the piezoelectric element 18) do not influence capacitive voltages (e.g., voltages measured between top electrodes 16). Additionally or alternatively, in some embodiments the electrodes 16, 20 may be electrically shorted together when measuring capacitive voltage. In that circumstance, the piezoelectric voltage (e.g. voltages across the piezoelectric element 18) are zero and thus do not dominate the capacitive voltage. Additionally, because the electrodes 16, 20 are shorted together, either electrode 16, 20 may be used to measure the capacitive voltage independent of orientation of the sensor 12 (i.e., independent of which electrode 16, 20 is closer to the occupant).

Sensor data measured by the BCG units 22 and the ECG unit 26 may be combined to improve accuracy of biomedical signals such as heart rate and respiration rate. For example, mathematical (e.g., correlation) and signal-processing operations may be applied to the different signals to improve performance. Additionally, the BCG units 22 and the ECG unit 26 may have different noise sensitivity due to different, independent physical properties. For example, the ECG unit 26 may not be affected by vibration noise, and the BCG units 22 may not be affected by external electric fields. Accordingly, the biomedical signals generated from both piezoelectric sensor data and capacitive sensor data may have a correlation rate of more than 90% when compared to a reference sensor system. Additionally, by using the same sensors 12 to perform both piezoelectric and capacitive sensing, the sensors 12 may reduce overall system complexity and/or cost as compared to using individual sensors for each type of sensing.

Figure 4:
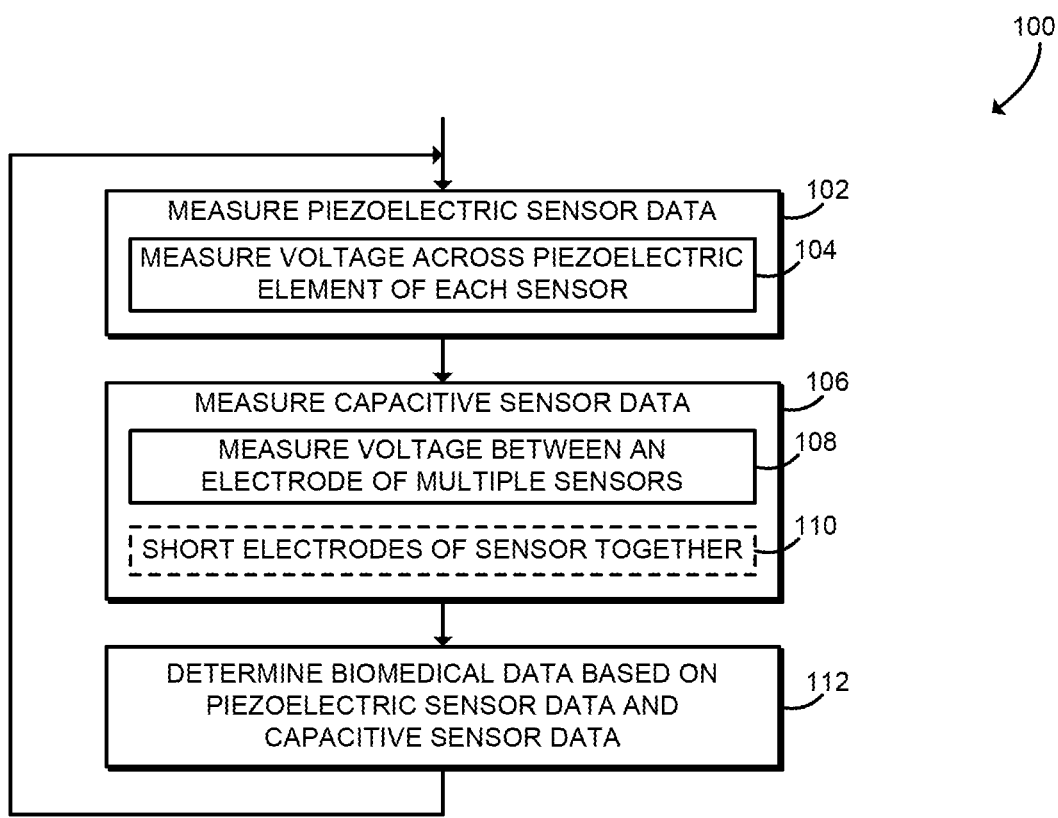
FIG. 4 is a simplified flow diagram illustrating a method for sensor sampling that may be executed by the sensor system of FIGS. 1-3.

In use, a method 100 as shown in FIG. 4 may be executed for measuring sensor data with the sensors 12. For example, the method 100 may be embodied as various instructions stored on a computer-readable media, which may be executed by a controller of the sensor system 14 (e.g., including or otherwise controlling the BCG unit 22 and/or the ECG unit 26) to cause the controller to perform the method 100. The computer-readable media may be embodied as any type of media capable of being read by the controller including, but not limited to, a memory, a data storage device, firmware devices, microcode, other memory or data storage devices.

The method 100 begins in block 102, in which the BCG units 22 measure piezoelectric sensor data. To measure the piezoelectric sensor data, in block 104 each BCG unit 22 measures voltage across the piezoelectric element 18 of each sensor 12. The BCG unit 22 may measure the voltage using the electrodes 16, 20 of each sensor 12. As described above, the sensor data measured by each BCG unit 22 may be indicative of biomedical data such as a heart rate or respiration rate of an occupant of the vehicle support 10. For example, the sensor data may be indicative of micro movements caused by blood pulsations. As another example, the sensor data measured by each BCG unit 22 may be indicative of sound vibrations experienced by the sensor 12.

In block 106, the ECG unit 26 measures capacitive sensor data. To measure the capacitive sensor data, in block 108 the ECG unit 26 measures voltage between one electrode (e.g., the top electrode 16 or the bottom electrode 20) of multiple sensors 12. For example, referring to FIG. 3, in an illustrative embodiment, the ECG unit 26 may measure voltage between the electrode 16 of the sensor 12a and the electrode 16 of the sensor 12b. In some embodiments, in block 110, the electrodes 16, 20 of the sensor 12 may be shorted together. As described above, shorting the electrodes 16, 20 may cause the piezoelectric voltage to be zero, and may make measurement of the capacitive voltage independent of the relative orientation of the electrodes 16, 20. As described above, the sensor data measured by the ECG unit 26 indicative of voltage differences between different locations on the occupant's skin, which may be indicative of biomedical data such as the heart rate and/or respiration rate of the user.

In block 112, biomedical data is determined based on both the capacitive sensor data and the piezoelectric sensor data. The biomedical data may be embodied as, for example, heart rate or respiration rate of the occupant of the vehicle support.

As described above, determining the biomedical data based on both the capacitive sensor data and the piezoelectric sensor data may improve correlation to a reference sensor system or otherwise improve performance. After combining the sensor data, the method 100 loops back to block 102 to continue monitoring piezoelectric sensor data and capacitive sensor data.

The following numbered clauses include embodiments that are contemplated and non-limiting:

Clause 1. An occupant support including:
a vehicle seat; and
a sensor system coupled to the vehicle seat and configured to provide biometric data of an occupant of the vehicle seat.

Clause 2. The occupant support of clause 1, any other clause, or any combination of clauses, wherein the biometric data comprises piezoelectric sensor data and capacitive sensor data.

Clause 3. The occupant support of clause 2, any other clause, or any combination of clauses, wherein the sensor system comprises a first sensor including a first metallic electrode, a second metallic electrode, and a piezoelectric element positioned between the first metallic electrode and the second metallic electrode.

Clause 4. The occupant support of clause 3, any other clause, or any combination of clauses, wherein the piezoelectric sensor data comprises ballistocardiogram data or sound data.

Clause 5. The occupant support of clause 3, any other clause, or any combination of clauses, wherein the capacitive sensor data comprises electrocardiogram data.

Clause 6. The occupant support of clause 3, any other clause, or any combination of clauses, wherein the piezoelectric sensor data is indicative of a voltage across the piezoelectric element between the first metallic electrode and the second metallic electrode.

Clause 7. The occupant support of clause 3, any other clause, or any combination of clauses, wherein the capacitive sensor data is indicative of capacitive coupling between the first metallic electrode and the occupant of the vehicle seat.

Clause 8. The occupant support of clause 7, any other clause, or any combination of clauses, wherein the sensor system comprises a second sensor including a first metallic electrode, a second metallic electrode, and a piezoelectric element positioned between the first metallic electrode and the second metallic electrode; and Clause 9. The occupant support of clause 8, any other clause, or any combination of clauses, wherein the capacitive sensor data is indicative of a first voltage between the first metallic electrode of the first sensor and the first metallic electrode of the second sensor.

Clause 10. The occupant support of clause 8, any other clause, or any combination of clauses, wherein the first voltage is galvanically isolated from a second voltage across the piezoelectric element of the first sensor.

Clause 11. A method for measuring biometric data of an occupant of a vehicle seat, the method comprising: measuring piezoelectric sensor data with a sensor system coupled to the vehicle seat, wherein the sensor system comprises a first sensor including a first metallic electrode, a second metallic electrode, and a piezoelectric element positioned between the first metallic electrode and the second metallic electrode, and wherein the piezoelectric sensor data is indicative of voltage across the piezoelectric element.

Clause 12. The method of clause 11, any other clause, or any combination of clauses, the method further comprising the step of measuring capacitive sensor data with the sensor system, wherein the capacitive sensor data is indicative of capacitive coupling between the first metallic electrode and the occupant of the vehicle seat.

Clause 13. The method of clause 12, any other clause, or any combination of clauses, wherein measuring the capacitive sensor data comprises shorting the first metallic electrode and the second metallic electrode.

Clause 14. The method of clause 12, any other clause, or any combination of clauses, further comprising combining the piezoelectric sensor data and the capacitive sensor data to generate biomedical data of the occupant of the vehicle seat.

The invention claimed is:

1. An occupant support including:
a vehicle seat; and
a sensor system coupled to the vehicle seat and configured to provide biometric data of an occupant of the vehicle seat, wherein the biometric data comprises piezoelectric sensor data and capacitive sensor data;
wherein the sensor system comprises a first sensor including a first metallic electrode, a second metallic electrode, and a piezoelectric element positioned between the first metallic electrode and the second metallic electrode; and
wherein the sensor system is configured to measure the capacitive sensor data when the first metallic electrode and the second metallic electrode are shorted together.

2. The occupant support of claim 1, wherein the piezoelectric sensor data comprises ballistocardiogram data or sound data.

3. The occupant support of claim 1, wherein the capacitive sensor data comprises electrocardiogram data.

4. The occupant support of claim 1, wherein the piezoelectric sensor data is indicative of a voltage across the piezoelectric element between the first metallic electrode and the second metallic electrode.

5. The occupant support of claim 1, wherein the capacitive sensor data is indicative of capacitive coupling between the first metallic electrode and the occupant of the vehicle seat.

6. The occupant support of claim 1, wherein:
the sensor system comprises a second sensor including a first metallic electrode, a second metallic electrode, and a piezoelectric element positioned between the first metallic electrode and the second metallic electrode; and
the capacitive sensor data is indicative of a first voltage between the first metallic electrode of the first sensor and the first metallic electrode of the second sensor, wherein the first voltage is indicative of a difference of capacitive coupling between the each of the first metallic electrodes and the occupant of the vehicle seat.

7. The occupant support of claim 6, wherein the first voltage is galvanically isolated from a second voltage across the piezoelectric element of the first sensor.

8. A method for measuring biometric data of an occupant of a vehicle seat, the method comprising:
measuring piezoelectric sensor data with a sensor system coupled to the vehicle seat, wherein the sensor system comprises a first sensor including a first metallic electrode, a second metallic electrode, and a piezoelectric element positioned between the first metallic electrode and the second metallic electrode, and wherein the piezoelectric sensor data is indicative of voltage across the piezoelectric element; and
measuring capacitive sensor data with the sensor system, wherein the capacitive sensor data is indicative of capacitive coupling between the first metallic electrode and the occupant of the vehicle seat, wherein measuring the capacitive sensor data comprises shorting the first metallic electrode and the second metallic electrode.

9. The method of claim 8, further comprising combining the piezoelectric sensor data and the capacitive sensor data to generate biomedical data of the occupant of the vehicle seat.

\* \* \* \* \*